(12) United States Patent
Hench et al.

(10) Patent No.: US 6,190,684 B1
(45) Date of Patent: *Feb. 20, 2001

(54) INJECTABLE BIO-ACTIVE GLASS IN A DEXTRAN SUSPENSION

(75) Inventors: Larry L. Hench, London (GB); Jon K. West; Guy LaTorre, both of Gainesville, FL (US); June Wilson, London (GB); William Toreki, III; Christopher Batich, both of Gainsville, FL (US)

(73) Assignee: University of Florida Research Foundation, Inc., Gainesville, FL (US)

( * ) Notice: Under 35 U.S.C. 154(b), the term of this patent shall be extended for 0 days.

This patent is subject to a terminal disclaimer.

(21) Appl. No.: 09/198,114

(22) Filed: Nov. 23, 1998

Related U.S. Application Data

(63) Continuation-in-part of application No. 08/657,713, filed on May 30, 1996, now Pat. No. 5,840,290.

(51) Int. Cl.$^7$ .............................. A61F 2/02; A61K 9/50; B32B 5/16
(52) U.S. Cl. .................. 424/423; 428/402; 428/402.24; 523/115
(58) Field of Search ................... 424/423, 499; 428/402, 402.24; 523/114, 115

(56) References Cited

U.S. PATENT DOCUMENTS

| 5,410,016 | 4/1995 | Hubbell et al. . |
| 5,840,290 | 11/1998 | Hench et al. . |

*Primary Examiner*—Carlos A. Azpuru
(74) *Attorney, Agent, or Firm*—Burns, Doane, Swecker & Mathis, L.L.P.

(57) ABSTRACT

The present invention relates to injectable suspensions of bio-active glass and dextran or a dextran derivative for the repair of soft tissue or hard bone in mammals, especially humans. In one embodiment, the dextran derivatives include free radical polymerizable groups, which can be polymerized following injection into a patient.

15 Claims, No Drawings

INJECTABLE BIO-ACTIVE GLASS IN A DEXTRAN SUSPENSION

This application is a continuation-in-part application of U.S. Ser. No. 08/657,713, filed May 30, 1996, now U.S. Pat. No. 5,840,290.

This invention was made with government support under contract number F49620-92-JO351, awarded by a grant from the U.S. Air Force. The government has certain rights in the invention.

BACKGROUND OF THE INVENTION

It has been common practice in plastic, otolaryngological and other surgeries for many years to inject or place within tissues a variety of artificial substances to repair or reconfigure anatomic structures. For example, Teflon polytetrafluoroethylene) particles have been introduced into the vocal cords and more recently into periureteral and periurethral tissues with mixed results. Disadvantages associated with this procedure include long-term progressive foreign body reactions and migration and distant embolism associated with very small particles. Considerable research has been conducted to discover substitutes for Teflon and other conventionally employed artificial materials.

Bio-active glasses have been utilized as bone replacement materials in a variety of reconstructive surgical techniques. These glasses have been shown to develop a strong bond with hard tissue because of a series of ion exchange reactions between the implant surface and body fluids that result in the formation of a biologically active calcium phosphate film at the implant tissue interface. See Hench et al, *J. Biomed. Mater. Res.*, Vol. 5, pp. 117–141 (1971), and Hench et al, *J. Biomed. Mater. Res.*, Vol. 7, pp. 25–42 (1973). Bio-active glasses have also been shown to form firm bonds with soft tissue. See Wilson, et al, *J. Biomed. Mater. Res.*, Vol. 15, pp. 805–817 (1981); Wilson and Merwin, *J. Biomed. Mater. Res.: Applied Biomaterials*, Vol. 22, No. A2, pp. 159–177 (1988); and Wilson, Low et al, *Biomaterials and Clinical Applications*, Ed. by Pizzoferrato et al, Elsevier Science Publishers B. V., Amsterdam (1987).

Certain bio-active and bio-compatible glasses and glass-ceramics, e.g., those described in U.S. Pat. Nos. 4,159,358; 4,234,972; 4,103,002; 4,189,325; 4,171,544; 4,775,646; 4,851,046, and 5,074,916 (all incorporated herein by reference), have been shown to develop a unique, strongly adherent, chemical bond with hard tissue (bone) tissue due to the influence on hydroxyapatite of the biologically active calcium phosphate film generated in situ by ion-exchange reactions between the glass or glass-ceramic surface and body fluids. This influence results in a strong fixation of the glass or glass-ceramic to the bone surface. Although as noted above, a variety of such glasses have been shown to bond to various soft tissues, it has been found that several of these glasses result in the formation of an exceptionally thin (i.e., no more than about 1–3 fibers thick), but adherent collagen film which strongly adheres the glass to soft tissue without concomitant adverse side effects.

Failure to observe soft tissue bonding of some glasses was a consequence of inappropriate preparation of material and selection of inappropriate tissue sites, e.g., muscle. When the glass implant is successfully immobilized in appropriate soft tissue during the experimental period and when proper histological specimens are made, soft tissue adhesion to some glasses can be confirmed and evaluated. These particular glass compositions have also been found to advantageously become encapsulated with a thin (i.e., no more than about 1–3 fibers thick) layer of collagen after implantation.

SUMMARY OF THE INVENTION

The present invention is directed to pharmaceutically acceptable fluid compositions particularly adapted for injection via a surgical needle into an animal, and methods of treatment using the compositions. The compositions include a suspension of a bio-active and bio-compatible glass particulate composition and dextrans or dextran derivatives having an average molecular weight of about 10,000 to about $2\times10^6$.

DETAILED DESCRIPTION OF THE INVENTION

The term "fluid" as used herein means any flowable and injectable liquid composition, including highly viscous compositions sometimes referred to as "pastes."

As used herein, the term "animal" means mammal, including a human. Unless specified otherwise the term "patient" means a human patient.

The term "pharmaceutically acceptable" as used herein is consistent with the art and means compatible with the other ingredients of a pharmaceutical composition and not deleterious to the recipient thereof.

The term "surgical needle" means any needle adapted for delivery of the fluid compositions of the present invention into a selected anatomical structure including a barrel type injector without a needle.

The term "anatomic structure" refers to any site or locus composed of hard tissue (bone) and/or soft tissue within the body of an animal.

The term "anatomic integrity" refers to the desired size, shape or configuration of a particular anatomic structure after bonding therewith of the particulate glass phase of the composition of the present invention.

The term "homogenous" as used herein is intended to include all compositions not subject to preferential extrusion of one or more of the components when injected into an animal.

Anatomic structures treatable according to the method of the present invention include, but are not limited to, vocal cords, periurethral tissue, periureteral tissue, maxilla, mandible, temporomandibular joint, chin, zygomatic arch, nose, ear, tooth root canal, tooth pulp caps, dental restoration, defects in bone, vertebral spaces, articulating joints, urethra, and subcutaneous and intradermal soft tissues. In addition, the compositions of the present invention are useful in treating:

Geneto-urinary indications including vesico-uretal (Renal) reflux, stress incontinence, post-prostatectomy stress incontinence, intrinsic sphincter deficiency, efferent limb incompetence, etc.

Gastro-enterological indications including gastro-esophageal reflux, gastric banding, fecal incontinence, etc.

Otolaryngologic indications including unilateral vocal cord paralysis, velopharyngeal incompetence, adductor laryngeal dystonia (spastic dysphonia), glottic insufficiency, etc.

Dermatologic indications including cutaneous contour deficiencies, wrinkle correction (e.g., glabellar furrows, nasolabial lines), depressed scars (due to e.g., acne, trauma, prior surgery, steroid- or disease induced areas of atrophy, post-rhinoplasty irregularities, depressed skin grafts), etc.

Vascular indications including sclerotherapy for peripheral vascular disorders, etc.

As noted above in the discussion of the background of this invention, bio-active and bio-compatible material, especially ceramic and glass material, are known in the art of medicine as useful in the restoration of bone and soft tissue. This art is discussed extensively in *Introduction to Bioceramics*, Ed., L. L. Hench and J. Wilson, especially chapter 1, World Scientific, London (19**). The bio-active glass materials for use in the compositions and methods described herein can be selected on the basis that they:

(a) form strong adherent bonds comprising a thin layer of collagen at a glass/soft tissue interface upon injection in the animal;

(b) form strong adherent bonds comprising a layer of collagen no more than about 1–3 fibers thick;

(c) become encapsulated after injection in the animal with a collagen layer attached by chemical and mechanical bonding to the bio-active surface;

(d) do not after injection into the animal contribute to the formation of excess scar tissue, giant cells or acute inflammatory cells; and do not cause long lasting foreign body reactions.

Bioactive glasses are any glass capable of forming hydroxyapatite after exposure to simulated body fluid. For example, bio-active and bio-compatible glasses having the following weight percent compositions give satisfactory results when utilized as the particulate glass.

| Component | Mole Percentage |
|---|---|
| $SiO_2$ | 40–86 |
| CaO | 15–46 |
| $Na_2O$ | 0–35 |
| $P_2O_5$ | 1–8 |
| $CaF_2$ | 0–25 |
| $B_2O_3$ | 0–10 |

The bio-active particulate glass used in the present invention may be prepared according to the methods of the art such as taught in U.S. Pat. Nos. 4,159,358; 4,234,972; 4,103,002; 4,189,325; 4,171,544; 4,775,646; 4,851,046, and 5,074,916. For example, the raw materials (e.g., $SiO_2$, CaO, $Na_2O$ and $P_2O_5$) are mixed in a Nalgene (trademark) plastic container on a ball mill for four hours. The mix is then melted in a platinum crucible at 1350° C. and homogenized for 24 hours. The molten glass is poured into distilled, deionized water to produce a glass frit. The frit is ground in a mortar and pestle and passed through ASTM sieves to produce the required particle size range. Particle size in accordance with the present invention is measured by scanning electron microscope (SEM) or laser light scattering techniques. The particles of bioactive glass may be spherical and smooth or rough and irregular. A preferred size range for the particles is between about 10 and 350 microns, more preferably, between about 90 and 250 microns, and, most preferably, between 90 and 150 microns.

The following compositions of bio-active glasses, known by the trademark "Bioglass" licensed to US Biomaterials, One Progress Boulevard, #23, Alachua, Fla., 32615, have been found to yield particularly good results and are, therefore, preferred.

TABLE 1

Bioglass (Trademark) Bio-active Glass Compositions in Mole %

| Composition | $SiO_2$ | $Na_2O$ | CaO | $P_2O_5$ |
|---|---|---|---|---|
| 45S5 | 46.1 | 24.4 | 26.9 | 2.6 |
| 52S4.6 | 52.1 | 21.5 | 23.8 | 2.6 |
| 55S4.3 | 55.1 | 20.1 | 22.2 | 2.6 |
| 60S3.8 | 60.1 | 17.7 | 19.6 | 2.6 |

Suitable carriers include dextrans, which are polysaccharides of D-glucose and are commercially produced by *Leuconostoc mesenteroides* and *L-dextranicum* bacteria. Dextrans have been widely used as plasma substitutes and blood extenders and are considered fully bio-compatible and are metabolizable. Dextrans are available in a wide range of average molecular weights varying from 4,000 to 40,000,000 Daltons and varying in rates of resorption in vivo from about two to twenty days depending on their molecular weight. The use of dextran derivatives, such as dextran phosphate and sulfate, with bio-active glass is also within the scope of the present invention.

In one embodiment, the derivatives are free radical-polymerizable, preferably photopolymerizable derivatives, such as acrylates. By using these materials, the composition can be injected as a viscous liquid, and polymerized in situ to form a solid material. The dextran can be selected to degrade at a rate which approximates ingrowth of new bone or tissue. Those compositions that include free radical polymerizable groups may also include polymerization initiators, such as photoinitiators such as benzoin ethers, and thermally activatable initiators, such as azobisisobutyronitrile (AIBN) and di-t-butyl ether. Free radical polymerization initiators, and conditions for carrying out free radical polymerizations, are well known to those of skill in the art.

Dextrans and dextran derivatives useful in the present invention have molecular weights in the range of about 10,000 to about $2\times10^6$ Daltons preferably in the range of about 35,000 to about 150,000, and most preferably about 74,000.

In addition to bio-active glass, dextrans or dextran derivatives, and sterilized deionized water, the composition of the present invention optionally contain excipients used in the pharmaceutical art to improve its performance and extend its shelf life. The excipients include, but are not limited to, preservative, coloring, flow enhancing, and suspension enhancing agents. Other acceptable carriers include cellulose and its derivatives, hyaluronan and its derivatives, glycogen, glycerol and its derivatives, fatty acid triglycerides such as oils of corn and soybean, methacrylated and succinylated collagens, dextrose, maltose, lactose, and other sugar derivatives, phospholipids, heparin, polyvinyl pyrrolidone, polyethylene glycol and other biodegradable, polymerizable hydrogels known to those of skill in the art, for example, those described in U.S. Pat. No. 5,410,016 to Hubbell et al., the contents of which are hereby incorporated by reference. Any of these may optionally include free radical polymerizable, preferably photopolymerizable groups.

The composition can optionally include bioactive agents, such as growth factors, antivirals, antibacterials, anti-inflammatories, immunosuppressants, analgesics, vascularizing agents, cell adhesion molecules (CAM's), bone morphologenic proteins (BMP's), anticoagulants, healing promotion agents, and topical anesthetics. Example of anti-inflammatories include corticosteroids, hydrocortisone (anti-inflammatory agents), and nonsteroidal antinflammatory drugs. Examples of topical anesthetics include benzocaine and lidocaine. Examples of suitable growth factors include TGF-β, basic fibroblast growth factor (bFGF), epithelial growth factor (EGF), transforming growth factors α and β (TGF α and β), platelet-derived growth factor (PDGF), and vascular endothelial growth factor/vascular permability factor (VEGF/VPF).

The fluid compositions may be conveniently prepared by dissolving dextran or a suitable dextran derivative in water (preferably sterile and deionized) to form a solution, preferably a viscous solution, suitable for injection. The ratio of dextran to water will vary according to the molecular weight of the dextran, but will be in the range of about 50 g to about 150 g of dextran to 100 mL of water. The viscous aqueous dextran solution can then be mixed with bio-active glass particles in the ratio of about 35:65 to about 65:35% by wt. glass to dextran to form an injectable fluid. The composition preferably includes at least 50 percent by volume, and, more preferably, greater than 70 percent by volume, of glass to carrier (dextran/water).

Because the viscosity and, hence injectability, is a function of the ratio of glass to dextran, this ratio will vary according to the application and the preference of the medical practitioner. The fluid composition can be sterilized by heating at about 120° C. to 135° C. for a minimum of about 30 to about 60 min, cooled under sterile conditions, then stored under sterile conditions. Further, the fluid can be thinned with sterile water or some other suitable liquid according to the application and preference of the medial practitioner.

The compositions can be administered via injection to any suitable site in a patient. The injection can be performed, for example, directly into a tooth or other bone defect, intramuscularly, intraperitoneally, or subcutaneously. For example, the fluid compositions may be injected using a standard medical syringe and needle (16 to 23 gauge is typical) under the skin of a patient into an area of soft tissue or bone in need of repair or augmentation. The amount of composition injected is according to the professional judgement of the medical practitioner treating the patient. After injection, the dextran or the dextran derivative will begin to degrade and be removed from the site by phagocytosis. Degradation and removal will be essentially complete in about two to about twenty days depending on the molecular weight of the dextran. That is, lower molecular weight dextran degrades quicker than high molecular weight dextran. The bio-active glass particles bond to the soft tissue site and create a long lasting tissue augmentation. In a hard tissue site, the glass particles will react with and bond to existing bone and induce the formation of new bone which will infiltrate the site.

In one embodiment, following injection, the dextran or suitable derivatives thereof are polymerized, therefore maintaining the structural integrity of the filled void. Preferably, the polymerized material includes bioactive agents which help promote healing, such that they are released as the dextran or derivative thereof degrades, to help promote healing.

The following examples are offered as illustrations of the present invention and are not to be construed as limitations thereof.

EXAMPLE 1

Dextran of an average molecular weight of about 74,000 to about 35,000 Daltons (3.5 g) is stirred into deionized water for injection (5.0 mL) to form a viscous solution. This dextran solution (5.0 mL) is then mixed with Bioglass (trademark) composition 45S5 (5.0 cc), having a particle size of about 125 μm to about 106 μm to form a 50:50 (dextran:bioactive glass) suspension of uniform consistency. This suspension is sterilized by heating at 125° C. for 30 minutes, cooled and stored in a pathogen free environment. The sterile suspension is loaded into a sterile 3 cc syringe fitted with a 35 mm, 18 gauge needle (maintaining sterile conditions) and injected into subcutaneous soft tissue of a mouse.

EXAMPLE 2

An injectable suspension is prepared as in Example 1 except that benzyl alcohol is added as a preservative at the rate of 0.05% % by weight prior to storing under sterile conditions.

EXAMPLE 3

An injectable suspension is prepared as in Example 1 except that the composition of the bioactive glass is Bioglass 52S4.6:

EXAMPLE 4

The evaluation of dextran as an injectable vehicle was accomplished by injecting a series of different molecular weight dextrans (74,000, 150,000 and 2,000,000 Daltons, supplied by Sigma Scientific, St. Louis, Mo.) and deionized water (DI) to achieve a desired viscosity. This solution was then mixed with Bioglass (trademark) 45S5 particles and injected onto a glass microscope slide ten times through an 18 gauge needle using a 1 cc tuberculin syringe.

The following table summarizes the results of the evaluation of dextran for injectable systems:

TABLE 2

| MW Dextran | Vol DI $H_2O$ | Vol Glass | Wt. Dextran/Vol Dextran/Injectability of 1 cc (%) |
|---|---|---|---|
| 74,000 | 5.0 g./5.0 cc | 5.0 cc/5.0 cc | hard to inject 100% |
| 74,000 | 4.0 g./5.0 cc | 5.0 cc/5.0 cc | more easily inj. 100% |
| 74,000 | 3.5 g./5.0 cc | 5.0 cc/5.0 cc | easily inj. 100% |
| 150,000 | 4.0 g./5.0 cc | 5.0 cc/5.0 cc | did not inj. well <50% |
| 150,000 | 3.5 g./5.0 cc | 5.0 cc/5.0 cc | hard to inj. <80% |

The results show that the 74,000 Daltons dextran (3.5 gr in 5.0 cc deionized water) with a 50% by volume load of glass particles was injectable through an 18 gauge needle. This same mixture could not be reliably injected through a 19 gauge needle with the same 50% by volume load of glass particles. Injection through a 19 gauge needle is possible with similar mixtures of both glycerine and hylan as presented previously.

EXAMPLE 5

Partial laryngeal paresthesia (i.e., resulting from laryngeal polyp removal or cancer resection) can be treated by augmenting the vocal cord on the affected side in order to establish better function. The spherical glass particles (with carrier) are injected through a needle into the tissue of the vocal fold on the affected side.

EXAMPLE 6

Stress incontinence can be treated by introducing a catheter through a cystoscope and inserting a needle into the submucosal tissue at or above the level of the external urinary sphincter. Repeated injections, i.e., four injections, of the spherical glass particles (with carrier) can be made, one injection at each of the following positions: 3, 6, 9, and 12 o'clock.

EXAMPLE 7

Vesico-ureteric reflux can be treated by introducing a catheter through a cystoscope and inserting a needle into the lamina propria behind the submusosal ureter. The spherical glass (with carrier) is then injected.

We claim:

1. A pharmaceutically acceptable fluid composition particularly adapted for injection via a surgical needle into an animal, comprising a suspension or dispersion of bio-active and bio-compatible glass particles and dextrans or dextran derivatives having an average molecular weight of about 10,000 to about $2 \times 10^6$.

2. The composition of claim 1, wherein the bio-active glass is of the following composition:

| Component | Mole Percentage |
|-----------|-----------------|
| $SiO_2$ | 40–86 |
| CaO | 15–46 |
| $Na_2O$ | 0–35 |
| $P_2O_5$ | 1–8 |
| $CaF_2$ | 0–25 |
| $B_2O_3$ | 0–10. |

3. The composition of claim 1, wherein the dextran derivatives include free radical-polymerizable groups.

4. The composition of claim 1, further comprising a free radical polymerization initiator.

5. A method for treating geneto-urinary indications including vesico-uretal (Renal) reflux, stress incontinence, post-prostatectomy stress incontinence, intrinsic sphincter deficiency, and efferent limb incompetence, comprising contacting an animal with the composition of claim 1.

6. The method of claim 5, wherein the dextran derivatives include free radical-polymerizable groups, further comprising polymerizing the derivatives after contacting the animal with the composition.

7. A method for treating gastro-enterological indications including indications including gastro-esophageal reflux, gastric banding, and fecal incontinence, comprising contacting an animal with the composition of claim 1.

8. The method of claim 7, wherein the dextran derivatives include free radical-polymerizable groups, further comprising polymerizing the derivatives after contacting the animal with the composition.

9. A method for treating otolaryngologic indications including unilateral vocal cord paralysis, velopharyngeal incompetence, adductor laryngeal dystonia (spastic dysphonia), and glottic insufficiency comprising contacting an animal with the composition of claim 1.

10. The method of claim 9, wherein the dextran derivatives include free radical-polymerizable groups, further comprising polymerizing the derivatives after contacting the animal with the composition.

11. A method for treating dermatologic indications including cutaneous contour deficiencies, wrinkle correction, and depressed scars comprising contacting an animal with the composition of claim 1.

12. The method of claim 11, wherein the dextran derivatives include free radical-polymerizable groups, further comprising polymerizing the derivatives after contacting the animal with the composition.

13. A method for treating vascular indications including sclerotherapy for peripheral vascular disorders comprising contacting an animal with the composition of claim 1.

14. The method of claim 13, wherein the dextran derivatives include free radical-polymerizable groups, further comprising polymerizing the derivatives after contacting the animal with the composition.

15. A method for repair, replacement, reconfiguration, reconstruction or augmentation of selected soft tissue and/or hard tissue (bone) anatomic structures in a patient in need thereof comprising injecting into the soft tissue and/or hard tissue (bone) of the patient a homogeneous suspension of bio-active and bio-compatible glass particulate composition having a particle size from about 250 micrometers to about 90 micrometers in an aqueous solution of dextrans or of dextran derivatives having an average molecular weight of about 10,000 to about 2,000,000 Daltons and optionally one or more preservative, coloring, flow enhancing, or suspension enhancing agents.

* * * * *